US012570633B2

(12) United States Patent
Liu et al.

(10) Patent No.: US 12,570,633 B2
(45) Date of Patent: Mar. 10, 2026

(54) PREPARATION METHOD FOR CDK4/6 INHIBITOR

(71) Applicant: CHIA TAI TIANQING PHARMACEUTICAL GROUP CO., LTD., Lianyungang (CN)

(72) Inventors: Guofeng Liu, Lianyungang (CN); Yong Wang, Lianyungang (CN); Meng Guo, Lianyungang (CN); Xiquan Zhang, Lianyungang (CN); Kaizhen Song, Lianyungang (CN); Jinhu Liu, Lianyungang (CN); Junshan Luo, Lianyungang (CN)

(73) Assignee: CHIA TAI TIANQING PHARMACEUTICAL GROUP CO., LTD, Lianyungang (CN)

( * ) Notice: Subject to any disclaimer, the term of this patent is extended or adjusted under 35 U.S.C. 154(b) by 601 days.

(21) Appl. No.: 18/011,759

(22) PCT Filed: Jun. 21, 2021

(86) PCT No.: PCT/CN2021/101246

§ 371 (c)(1),
(2) Date: Dec. 20, 2022

(87) PCT Pub. No.: WO2021/259203

PCT Pub. Date: Dec. 30, 2021

(65) Prior Publication Data

US 2023/0331699 A1 Oct. 19, 2023

(30) Foreign Application Priority Data

Jun. 22, 2020 (CN) ........................ 202010571393.7

(51) Int. Cl.
*C07D 401/14* (2006.01)

(52) U.S. Cl.
CPC .................................. *C07D 401/14* (2013.01)

(58) Field of Classification Search
CPC .................................................... C07D 401/14
USPC ......................................................... 544/295
See application file for complete search history.

(56) References Cited

U.S. PATENT DOCUMENTS

2008/0242694 A1 10/2008 D'Sidocky et al.

FOREIGN PATENT DOCUMENTS

| | | | | | |
|---|---|---|---|---|---|
| CN | 105111191 | A | | 12/2015 | |
| EP | 1 593 673 | A1 | | 11/2005 | |
| EP | 3643711 | A1 | | 4/2020 | |
| WO | 2009/144554 | A1 | | 12/2009 | |
| WO | 2010/075074 | A1 | | 7/2010 | |
| WO | 2012/040258 | A2 | | 3/2012 | |
| WO | WO-2016014904 | A1 | * | 1/2016 | ............. A61P 35/02 |
| WO | 2016/141881 | A1 | | 9/2016 | |
| WO | WO-2018045993 | A1 | * | 3/2018 | ............. A61P 35/00 |
| WO | 2019/148161 | A1 | | 8/2019 | |

OTHER PUBLICATIONS

English translation of WO 2018045993 A1, WIPO, published Mar. 15, 2018. (Year: 2018).*

Shendage et al., Highly Efficient Stereoconservative Amidation and Deamidation of a-Amino Acids, Organic Letters, 2004, vol. 6(21), pp. 3675-3678 (Year: 2004).*

Temple et al., Discovery of a novel 2,3-dimethylimidazo[1,2-a]pyrazine-6-carboxamide M4 positive allosteric modulator (PAM) chemotype, Bioorganic & Medicinal Chemistry Letters, Nov. 13, 2019, pp. 1-5 (Year: 2019).*

Sep. 18, 2021 Search Report issued in International Patent Application No. PCT/CN2021/101246.

* cited by examiner

*Primary Examiner* — Jeffrey H Murray
*Assistant Examiner* — Rilla Marie Samsell
(74) *Attorney, Agent, or Firm* — Oliff PLC

(57) ABSTRACT

A preparation method for a CDK4/6 inhibitor for a compound of formula (I):5-fluoro-4-(3-isopropyl-2-methyl-2H-indazol-5-yl)-N-(5-(piperazin-1-yl) pyrazol-2-yl)pyrimidine-2-amine. The preparation method has cheap and readily available starting materials and reagents, greatly simplified total reaction steps, shortened reaction time, improved total yield and a high purity of the key intermediate and final product, being suitable for industrial production.

20 Claims, No Drawings

PREPARATION METHOD FOR CDK4/6 INHIBITOR

CROSS-REFERENCE TO RELATED APPLICATIONS

The present application claims the benefit and priority to the Chinese Patent Application No. 202010571393.7 filed with National Intellectual Property Administration, PRC on Jun. 22, 2020, which is incorporated herein by reference in its entirety.

TECHNICAL FIELD

The present application relates to the field of drug synthesis, particularly to a method for preparing a CDK4/6 inhibitor, and more particularly to a method for preparing a compound of formula (I): 5-fluoro-4-(3-isopropyl-2-methyl-2H-indazol-5-yl)-N-(5-(piperazin-1-yl) pyrazol-2-yl)pyrimidine-2-amine.

BACKGROUND

The regulation of cell cycle is mainly affected by a series of serine/threonine kinases, which are also known as cyclin-dependent kinases (CDKs). They promote the progression of cell cycle, transcription of genetic information and normal division and proliferation of cells by binding to their corresponding regulatory subunit cyclins. CDK4/6 is a key regulator of cell cycle. It triggers the transition of cell cycle from the growth phase (G1 phase) to the DNA replication phase (S1 phase). In the process of cell proliferation, the complex formed by cyclin D and CDK4/6 can phosphorylate the retinoblastoma protein (Rb). Once the tumor suppressor protein Rb is phosphorylated, it can release transcription factor E2F to which it tightly binds in the unphosphorylated state. E2F activates further transcription to promote the cell cycle through the restriction point (R point) from G1 phase to S phase, thus entering the cell proliferation phase. Therefore, the inhibition of CDK4/6 and thus its inability to form cyclin D-CDK4/6 complex, can block the progression of cell cycle from G1 phase to S phase, thereby achieving the purpose of inhibiting tumor proliferation. In the estrogen receptor-positive (ER+) breast cancer (BC), CDK4/6 is frequently overactive and is a key downstream target for ER signaling. Preclinical data suggest that the dual inhibition of CDK4/6 and estrogen receptor (ER) signaling has a synergistic effect, and can inhibit the growth of estrogen receptor-positive (ER+) breast cancer (BC) cells in G1 phase. Patent No. WO2016141881 discloses a CDK4/6 inhibitor with a structure shown in formula (I). The compound of formula (I) has an $IC_{50}$ value less than 1 nM against CDK4/6, and has good tumor inhibitory activity against breast cancer, (I)

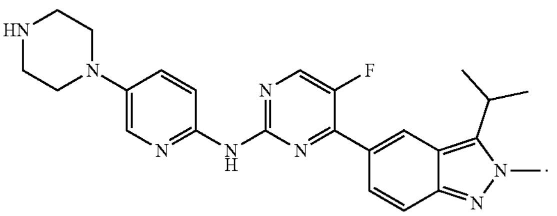

Patent No. WO2016141881 also discloses a method for preparing the compound of formula (I) by the following route:

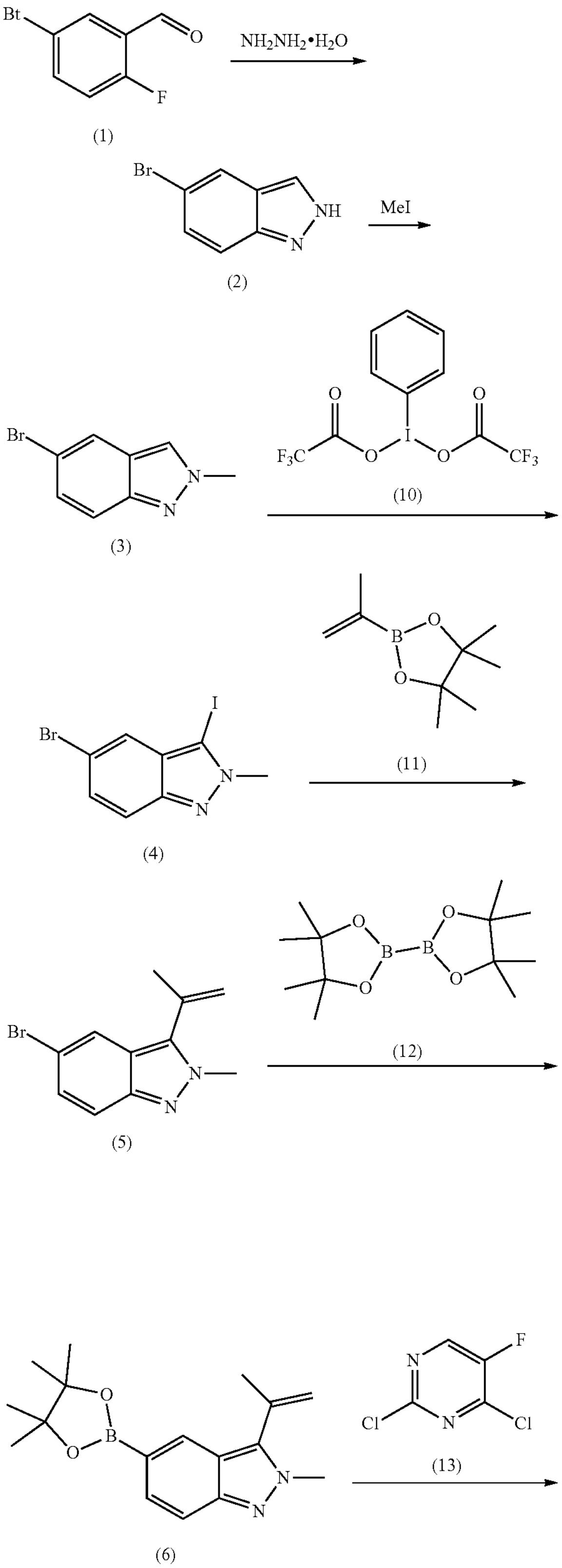

-continued

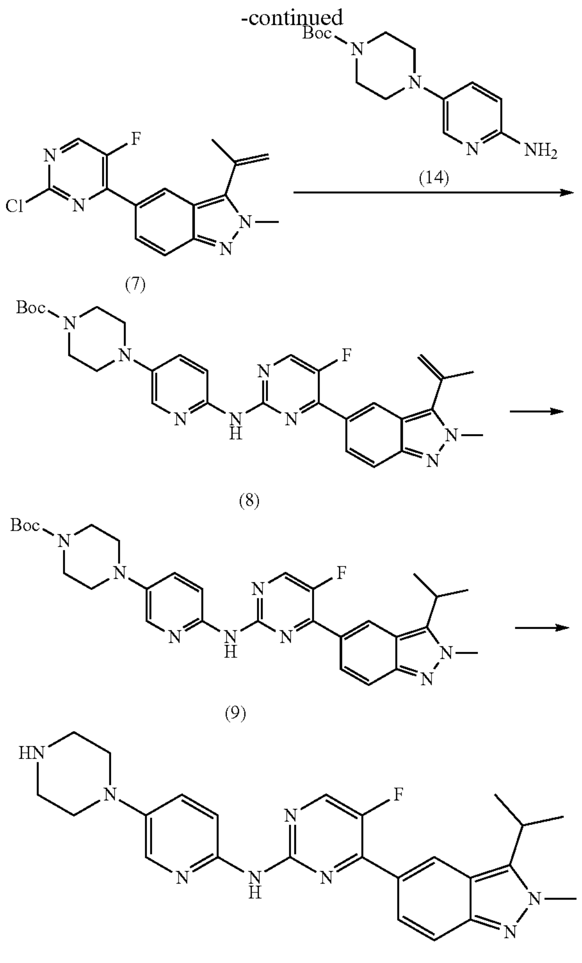

(14)

(7)

(8)

(9)

(I)

The process for preparing the compound of formula (I) described above has numerous disadvantages, including:

(i) The crude products of intermediate compound (2), compound (3), compound (4), compound (5), compound (6) and compound (7) are all oily substances, which need purification by silica gel column chromatography before use in the next reaction, and are therefore not suitable for industrial production.

(ii) The processes for preparing intermediate compound (5), compound (6), compound (7), compound (8) and compound (9) all use metal catalysts, and are not suitable for industrial production due to high process cost and complex post-treatment.

(iii) The structure of compound (8) contains too many N atoms capable of coordinating with metal, such that the reduction reaction thereof takes a long time, which also makes the process unsuitable for industrial production.

SUMMARY

The present application is intended to provide a new method for preparing the compound of formula (I), which is more suitable for industrial production. The reagents of the method are cost-efficient and readily available, the intermediates generated do not require silica gel column chromatography in the post-treatment, the operations are simple and convenient, the reaction time for each step is short, and the yield and purity are high.

In one aspect, the present application provides a method for preparing a compound of formula (I), comprising:

step 1: reacting compound SMA-1 with compound SMA-8 to give compound SMA-2;

step 2: reacting compound SMA-2 with hydrazine hydrate to give compound SMA-3;

step 3: subjecting compound SMA-3 to a methylation reaction to give compound SMA-4;

step 4: reacting compound SMA-4 with bis(pinacolato) diboron to give compound SMA-5;

step 5: reacting compound SMA-5 with compound SMA-9 to give compound SMA-6;

step 6: reacting compound SMA-6 with compound SMA-10 to give compound SMA-7; and step 7: reacting compound SMA-7 to give compound of formula (I).

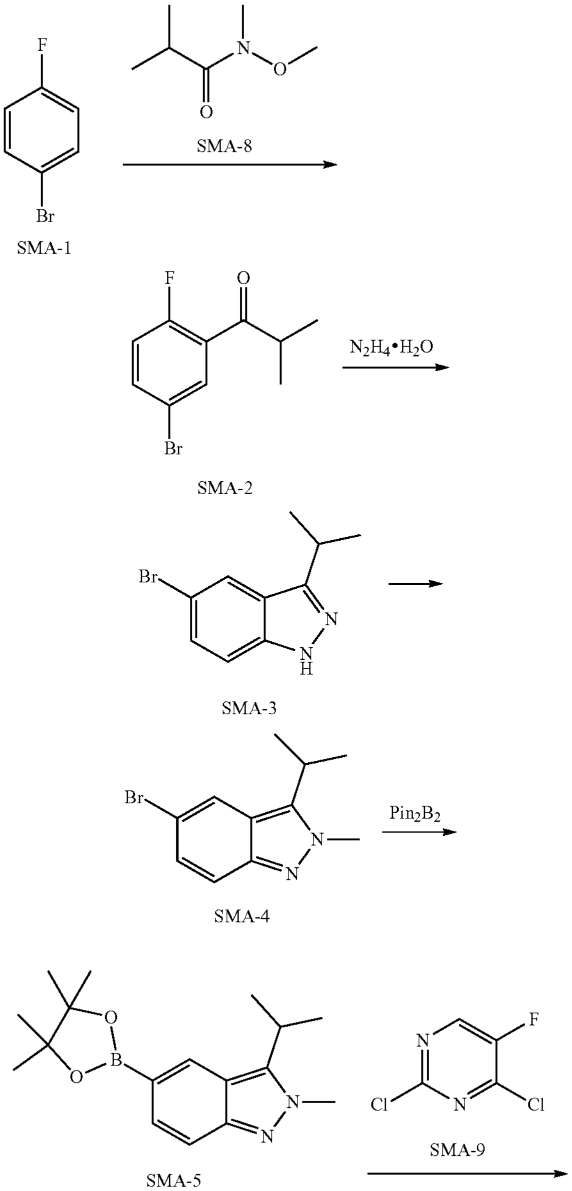

SMA-8

SMA-1

SMA-2

SMA-3

SMA-4

SMA-5

SMA-9

-continued

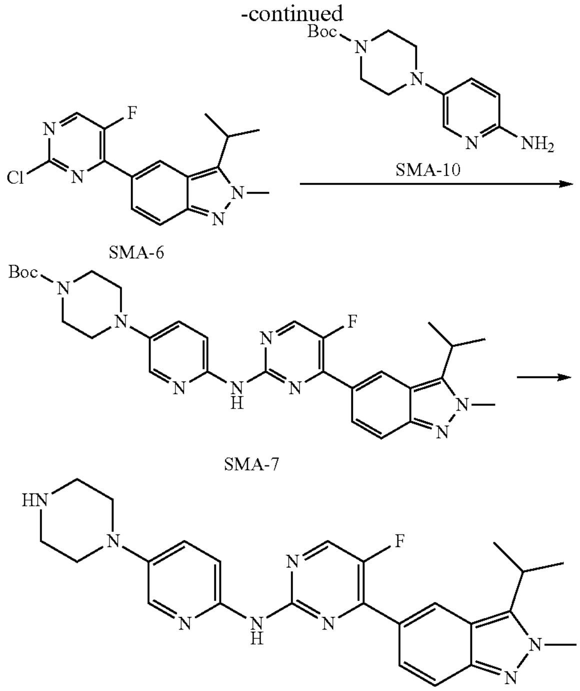

SMA-10

SMA-6

SMA-7

(1)

In some embodiments, step 1 described above is conducted in the presence of a solvent and a base. In some embodiments, the solvent in step 1 described above selected from one of or a mixed solvent of two or more of dichloromethane, tetrahydrofuran, dioxane, DMF, DMSO, acetonitrile, diethyl ether, isopropyl ether, methyl tert-butyl ether, 2-methyltetrahydrofuran, n-hexane and n-heptane, preferably one of or a mixed solvent of two or more of tetrahydrofuran, dioxane and n-heptane, and more preferably tetrahydrofuran.

In some embodiments, the base in step 1 described above is selected from the group consisting of n-butyllithium, tert-butyllithium, sodium tert-butoxide, potassium tert-butoxide, lithium diisopropylamide, lithium hexamethyldisilazide, sodium bis(trimethylsilyl)amide, sodium hydride and lithium hydroxide, preferably lithium diisopropylamide, n-butyllithium and lithium hexamethyldisilazide, and more preferably lithium diisopropylamide.

In some embodiments, the reaction temperature for step 1 described above is −75 to −20° C., preferably −75 to −50° C., and more preferably −75 to −65° C.

In some embodiments, the reaction time for step 1 described above is 2 to 10 hours, preferably 2 to 6 hours, and more preferably 3 to 5 hours.

In some embodiments, the molar ratio of compound SMA-1 to compound SMA-8 in step 1 described above is 1:(1-2), preferably 1:(1-1.5), and more preferably 1:(1-1.4). In some specific embodiments, the molar ratio of compound SMA-1 to compound SMA-8 in step 1 described above is about 1:1.33.

In some embodiments, the molar-to-volume ratio of compound SMA-1 to the solvent in step 1 described above is 1 mmol:(0.5-1.5) mL, preferably 1 mmol:(1-1.5) mL, and more preferably 1 mmol:(1-1.2) mL. In some specific embodiments, the molar-to-volume ratio of compound SMA-1 to the solvent in step 1 described above is about 1 mmol: 1 mL.

In some embodiments, the molar ratio of compound SMA-1 to the base in step 1 described above is 1:(1-3), preferably 1:(1.5-3), and more preferably 1:(1.5-2.1). In some specific embodiments, the molar ratio of compound SMA-1 to the base in step 1 described above is 1:2.

In some embodiments, step 1 described above comprises: dissolving compound SMA-1 and compound SMA-8 in the solvent to form a solution, and then adding the base for reaction to give compound SMA-2.

In some embodiments, step 1 described above further comprises: cooling the solution to −75 to −20° C., preferably −75 to −50° C., and more preferably −75 to −65° C. In some embodiments, step 1 described above further comprises: adding the base at a temperature of −65° C.

In some embodiments, step 1 described above further comprises: reacting for 3 hours after the addition of the base is completed.

In some embodiments, step 1 described above further comprises: adding an acid to the reaction solution for treatment after the reaction is completed. In some specific embodiments, the acid is hydrochloric acid (e.g., a 1 mol/L aqueous hydrochloric acid solution).

In some embodiments, step 1 described above further comprises: separating SMA-2 after adding the acid to the reaction solution for treatment.

In some specific embodiments, step 1 described above comprises: mixing SMA-1, SMA-8 and tetrahydrofuran, stirring for complete dissolution, cooling to an internal temperature of −75 to −65° C., adding lithium diisopropylamide with the internal temperature maintained below −65° C., and reacting for 3 hours with the internal temperature maintained at −75 to −65° C. after the addition; adding a 1 mol/L aqueous hydrochloric acid solution to the reaction solution, warming to room temperature after the addition, and separating the phases; extracting the aqueous phase with ethyl acetate, combining the organic phases, washing with water, drying over anhydrous sodium sulfate and filtering; and concentrating the filtrate to dryness at reduced pressure to give compound SMA-2.

In the present application, step 1 described above further comprises: reacting compound SMA-11 with compound SMA-12 to give compound SMA-8.

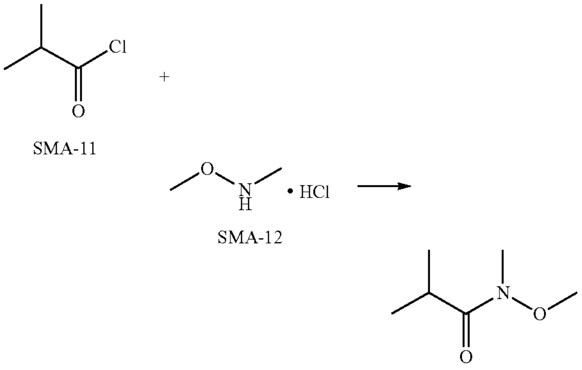

SMA-11

SMA-12

SMA-8

In some embodiments, the preparation of compound SMA-8 described above is conducted in the presence of a solvent and a base.

In some embodiments, the solvent for the preparation of compound SMA-8 described above is selected from the group consisting of ethyl acetate, dichloromethane, toluene, chloroform, 1,2-dichloroethane, n-hexane, diethyl ether and methyl tert-butyl ether, preferably dichloromethane and methyl tert-butyl ether, and more preferably dichloromethane.

In some embodiments, the base for the preparation of compound SMA-8 described above is selected from the group consisting of triethylamine, diisopropylethylamine, pyridine, 4-dimethylaminopyridine (DMAP), 1,8-diazabicycloundec-7-ene (DBU) and triethylenediamine, preferably triethylamine and diisopropylethylamine, and more preferably triethylamine. In some embodiments, the reaction temperature for the preparation of compound SMA-8 described above is 0-30° C., preferably 5-25° C., and more preferably 15-25° C. In some embodiments, the reaction temperature for the preparation of compound SMA-8 described above is about 25° C. In some embodiments, the reaction time for the preparation of compound SMA-8 described above is 0.5-5 hours, preferably 0.5-2 hours, and more preferably 1-2 hours.

In some embodiments, in the preparation of compound SMA-8 described above, the molar ratio of compound SMA-11 to compound SMA-12 is 1:(1-2), preferably 1:(1-1.5), and more preferably 1:(1-1.2). In some specific embodiments, the molar ratio of compound SMA-11 to compound SMA-12 is 1:1.

In some embodiments, in the preparation of compound SMA-8 described above, the molar-to-volume ratio of compound SMA-11 to the solvent is 1 mmol:(0.2-2) mL, preferably 1 mmol:(0.5-2) mL, and more preferably 1 mmol:(0.5-1) mL. In some specific embodiments, the molar-to-volume ratio of compound SMA-11 to the solvent is about 1 mmol: 0.5 mL. In some embodiments, in the preparation of compound SMA-8 described above, the molar ratio of compound SMA-11 to the base is 1:(1-3), preferably 1:(1.5-3), and more preferably 1:(1.5-2). In some specific embodiments, the molar ratio of compound SMA-11 to the base is about 1:2. In some embodiments, in the preparation of compound SMA-8 described above, compound SMA-12 is first mixed with the solvent (e.g., at a temperature of −5 to 5° C.), followed by the addition of a base (e.g., at a temperature below 5° C.) and subsequently SMA-11 (e.g., at a temperature below 5° C.).

In some embodiments, the preparation of compound SMA-8 described above comprises: dissolving SMA-12 in dichloromethane with the temperature maintained at −5 to 5° C.; adding triethylamine with the temperature maintained below 5° C.; adding SMA-11 with the temperature maintained below 5° C.; and after the addition, reacting the resulting mixture at room temperature for 1 hour. In some embodiments, the preparation of compound SMA-8 described above further comprises: treating with a base (e.g., sodium bicarbonate) after the reaction is completed.

In the present application, the compound SMA-8 in step 1 described above is also commercially available.

In some embodiments, step 2 described above is conducted in the presence of a solvent. In some embodiments, the solvent in step 2 described above is selected from the group consisting of ethylene glycol, N,N-dimethylformamide (DMF), dimethyl sulfoxide (DMSO), diphenyl ether, orthodichlorobenzene, sulfolane, trimethylbenzene, diethylene glycol dimethyl ether and N-methylpyrrolidone, preferably DMF and ethylene glycol, and more preferably ethylene glycol. In some embodiments, step 2 described above further comprises: removing water in the reaction process.

In some embodiments, step 2 described above comprises: reacting compound SMA-2 with hydrazine hydrate for a period of time, removing water, and then continuing the reaction.

In some embodiments, the reaction temperature for step 2 described above is 100-200° C., and preferably 150-200° C.

In some embodiments, step 2 described above comprises: reacting compound SMA-2 with hydrazine hydrate first at a temperature of 180-200° C. or at reflux, and later reacting at a temperature of 150° C. Specifically, there is a step of removing water between the two reactions. In some embodiments, the reaction time for step 2 described above is 2-15 hours, preferably 5-12 hours, and more preferably 10-12 hours.

In some embodiments, step 2 described above comprises: reacting compound SMA-2 with hydrazine hydrate first at a temperature of 180-200° C. or at reflux for 2 hours, and later reacting at a temperature of 150° C. for 10 hours. Specifically, there is a step of removing water between the two reactions.

In some embodiments, the molar ratio of compound SMA-2 to hydrazine hydrate in step 2 described above is 1:(1-3), preferably 1:(1.5-3), and more preferably 1:(1.5-2).

In some embodiments, the molar-to-volume ratio of compound SMA-2 to the solvent in step 2 described above is 1 mmol:(0.5-1.5) mL, preferably 1 mmol:(1-1.5) mL, and more preferably 1 mmol:(1-1.2) mL.

In some embodiments, step 2 described above comprises: reacting SMA-2 with hydrazine hydrate at reflux in the presence of ethylene glycol for 2 hours, removing water from the reaction system, and reacting at 150° C. for 10 hours to give compound SMA-3.

In some embodiments, step 2 described above further comprises: adding water to the reaction system after the reaction is completed to precipitate compound SMA-3; and further comprises: slurrying with purified water for treatment.

In some embodiments, step 3 described above is conducted in the presence of a methylating agent and a solvent.

In some embodiments, the methylating agent in step 3 described above is selected from the group consisting of iodomethane, dimethyl sulfate, dimethyl carbonate, methyl p-toluenesulfonate, methyl triflate, tetramethylammonium fluoride, trimethyl phosphate, trimethyloxonium tetrafluoroborate and 1-methyl-3-p-tolyltriazole, preferably iodomethane and trimethyloxonium tetrafluoroborate, and more preferably trimethyloxonium tetrafluoroborate.

In some embodiments, the solvent in step 3 described above is selected from one of or a mixed solvent of two or more of ethyl acetate, dichloromethane and acetone, and preferably one of or a mixed solvent of two of ethyl acetate and dichloromethane. In some specific embodiments, the solvent in step 3 described above is ethyl acetate followed by dichloromethane. In some embodiments, the solvent in step 3 described above is ethyl acetate.

In some embodiments, step 3 described above is conducted in the presence of the methylating agent, a base and the solvent.

In some embodiments, the base in step 3 described above is selected from the group consisting of potassium carbonate, sodium carbonate, sodium methoxide, sodium ethoxide, potassium bicarbonate, sodium bicarbonate, sodium hydroxide and potassium hydroxide, preferably sodium bicarbonate and sodium hydroxide, and more preferably sodium bicarbonate.

In some embodiments, the reaction temperature for step 3 described above is controlled at 10-30° C., preferably 20-30° C., and more preferably 25-30° C.

In some embodiments, the reaction time for step 3 described above is 5-12 hours, preferably 8-12 hours, and more preferably 8-10 hours. In some specific embodiments, the reaction time for step 3 described above is about 8 hours.

In some embodiments, step 3 described above comprises: reacting compound SMA-3 with trimethyloxonium tetrafluoroborate to give a tetrafluoroborate salt of compound SMA-4, and reacting the tetrafluoroborate salt of compound SMA-4 to give compound SMA-4.

In some embodiments, the step of reacting the tetrafluoroborate salt of compound SMA-4 to give compound SMA-4 described above can be conducted in the presence of a base (e.g., sodium bicarbonate).

In some embodiments, the preparation of the tetrafluoroborate salt of compound SMA-4 described above is conducted in the presence of a solvent selected from the group consisting of ethyl acetate and acetone, and preferably ethyl acetate.

In some embodiments, the preparation of the tetrafluoroborate salt of compound SMA-4 described above is conducted in the presence of a solvent selected from the group consisting of ethyl acetate and acetone, and preferably ethyl acetate.

In some embodiments, the step of reacting the tetrafluoroborate salt of compound SMA-4 to give compound SMA-4 described above is conducted in the presence of a solvent selected from the group consisting of dichloromethane and ethyl acetate, preferably dichloromethane, or preferably ethyl acetate.

In some embodiments, step 3 described above comprises: reacting compound SMA-3 with trimethyloxonium tetrafluoroborate in the presence of ethyl acetate to give a tetrafluoroborate salt of compound SMA-4, and reacting the tetrafluoroborate salt of compound SMA-4 in the presence of dichloromethane and a base to give compound SMA-4.

In some embodiments, step 3 described above comprises: reacting compound SMA-3 with trimethyloxonium tetrafluoroborate in the presence of ethyl acetate at a temperature of 25-30° C. to give a tetrafluoroborate salt of compound SMA-4, separating the tetrafluoroborate salt of compound SMA-4, and reacting the tetrafluoroborate salt of compound SMA-4 with sodium bicarbonate in the presence of dichloromethane and water to give compound SMA-4.

In some embodiments, the molar ratio of compound SMA-3 to the methylating agent in step 3 described above is 1:(1-3), preferably 1:(1-2), and more preferably 1:(1-1.2).

In some embodiments, the molar ratio of compound SMA-3 to the base in step 3 described above is 1:(1-5), preferably 1:(2-4), and more preferably 1:(2.5-3.5).

In some embodiments, step 4 described above is conducted in the presence of a catalyst, a base and a solvent.

In some embodiments, the catalyst in step 4 described above is selected from the group consisting of palladium acetate, 1,2-bis(diphenylphosphonyl) ethane palladium dichloride, 1,3-bis(diphenylphosphino) propane palladium dichloride, 1,4-bis(diphenylphosphino) butane palladium dichloride, bis(triphenylphosphine) palladium dichloride, bis(cyanophenyl) palladium dichloride, 1,1'-bis(diphenylphosphino) ferrocenepalladium dichloride and tris (dibenzylideneacetone) dipalladium, preferably bis(triphenylphosphine) palladium dichloride and 1,1'-bis (diphenylphosphino) ferrocenepalladium dichloride, and more preferably 1,1'-bis(diphenylphosphino) ferrocenepalladium dichloride.

In some embodiments, the base in step 4 described above is selected from the group consisting of sodium carbonate, potassium carbonate, cesium carbonate, sodium acetate, potassium acetate, sodium ethoxide, sodium tert-butoxide, potassium tert-butoxide, triethylamine, pyridine, piperidine and N-methylpiperidine, preferably potassium acetate and cesium carbonate, and more preferably potassium acetate.

In some embodiments, the solvent in step 4 described above is selected from one of or a mixed solvent of two or more of methanol, ethanol, isopropanol, tetrahydrofuran, dioxane, DMF, DMSO, toluene, ethylbenzene, ethylene glycol dimethyl ether, acetonitrile and water, preferably tetrahydrofuran and dioxane, and more preferably dioxane.

In some embodiments, the reaction temperature for step 4 described above is 80-120° C., preferably 85-105° C., and more preferably 90-105° C. In some specific embodiments, the reaction temperature for step 4 described above is 90-95° C.

In some embodiments, the reaction time for step 4 described above is 5-15 hours, preferably 8-12 hours, and more preferably 8-10 hours. In some specific embodiments, the reaction time for step 4 described above is about 9 hours.

In some embodiments, the molar ratio of compound SMA-4 to bis(pinacolato)diboron in step 4 described above is 1:(1-3), preferably 1:(1-2), and more preferably 1:(1-1.5).

In some embodiments, the molar ratio of compound SMA-4 to the catalyst in step 4 described above is 1:(0.001-0.01), preferably 1:(0.002-0.008), and more preferably 1:(0.004-0.006).

In some embodiments, the molar ratio of compound SMA-4 to the base in step 4 described above is 1:(1-3), preferably 1:(1-2), and more preferably 1:(1.5-2).

In some embodiments, the molar-to-volume ratio of compound SMA-4 to the solvent in step 4 described above is 1 mmol:(1-2) mL, preferably 1 mmol:(1-1.5) mL, and more preferably 1 mmol:(1.2-1.5) mL.

In some embodiments, step 4 described above comprises: reacting compound SMA-4 with bis(pinacolato)diboron in the presence of 1,4-dioxane, potassium acetate and 1,1'-bis (diphenylphosphino) ferrocenepalladium dichloride to give compound SMA-5.

In some embodiments, step 4 described above comprises: reacting compound SMA-4 with bis(pinacolato)diboron in the presence of 1,4-dioxane, potassium acetate and 1,1'-bis (diphenylphosphino) ferrocenepalladium dichloride at a reaction temperature of 90-95° C. for 9 hours to give compound SMA-5.

In some embodiments, step 5 described above is conducted in the presence of a catalyst, a base and a solvent.

In some embodiments, the catalyst in step 5 described above is selected from the group consisting of palladium acetate, 1,2-bis(diphenylphosphonyl) ethane palladium dichloride, 1,3-bis(diphenylphosphino) propane palladium dichloride, 1,4-bis(diphenylphosphino) butane palladium dichloride, bis(triphenylphosphine) palladium dichloride, bis(cyanophenyl) palladium dichloride, 1,1'-bis(diphenylphosphino) ferrocenepalladium dichloride and tris (dibenzylideneacetone) dipalladium, preferably bis(triphenylphosphine) palladium dichloride and 1,1'-bis (diphenylphosphino) ferrocenepalladium dichloride, and more preferably 1,1'-bis(diphenylphosphino) ferrocenepalladium dichloride.

In some embodiments, the base in step 5 described above is selected from the group consisting of sodium carbonate, potassium carbonate, cesium carbonate, sodium acetate, potassium acetate, sodium ethoxide, sodium tert-butoxide, potassium tert-butoxide, triethylamine, pyridine, piperidine and N-methylpiperidine, preferably cesium carbonate and potassium carbonate, and more preferably cesium carbonate.

In some embodiments, the solvent in step 5 described above is selected from one of or a mixed solvent of two or more of methanol, ethanol, isopropanol, tetrahydrofuran, dioxane, DMF, DMSO, toluene, ethylbenzene, ethylene glycol dimethyl ether, acetonitrile and water, preferably dioxane and toluene, and more preferably dioxane.

In some embodiments, the reaction temperature for step 5 described above is 80-120° C., preferably 85-105° C., and more preferably 90-105° C.

In some embodiments, the reaction time for step 5 described above is 5-15 hours, preferably 8-12 hours, and more preferably 10-12 hours.

In some embodiments, the molar ratio of compound SMA-5 to compound SMA-9 in step 5 described above is 1:(1-2), preferably 1:(1-1.5), and more preferably 1:(1-1.2).

In some embodiments, the molar ratio of compound SMA-5 to the catalyst in step 5 described above is 1:(0.005-0.05), preferably 1:(0.01-0.05), and more preferably 1:(0.01-0.03).

In some embodiments, the molar ratio of compound SMA-5 to the base in step 5 described above is 1:(1-3), preferably 1:(1-2), and more preferably 1:(1.5-2).

In some embodiments, the molar-to-volume ratio of compound SMA-5 to the solvent in step 5 described above is 1 mmol:(0.1-2) mL, preferably 1 mmol:(0.2-1) mL, and more preferably 1 mmol:(0.2-0.5) mL.

In some embodiments, step 5 described above comprises: reacting compound SMA-5 with compound SMA-9 in the presence of potassium carbonate, water and 1,1'-bis(diphenylphosphino) ferrocenepalladium dichloride at a temperature of 90-95° C. to give compound SMA-6.

In some embodiments, step 5 described above further comprises: adding a mixed solution of ethanol and water for treatment after the reaction is completed; further comprises: adding a solid separated after the treatment to a mixed system of water and dichloromethane for treatment; and still further comprises: separating an organic phase after the treatment, and treating the organic phase with anhydrous sodium sulfate and activated carbon.

In some embodiments, step 5 described above further comprises: purifying the compound SMA-6 with ethyl acetate.

In some embodiments, the step 6 described above is conducted in the presence of a catalyst, a base and a solvent.

In some embodiments, the catalyst in step 6 described above is selected from the group consisting of palladium acetate, 1,2-bis(diphenylphosphonyl) ethane palladium dichloride, 1,3-bis(diphenylphosphino) propane palladium dichloride, 1,4-bis(diphenylphosphino) butane palladium dichloride, bis(triphenylphosphine) palladium dichloride, bis(cyanophenyl) palladium dichloride, 1,1'-bis(diphenylphosphino) ferrocenepalladium dichloride and tris (dibenzylideneacetone) dipalladium, preferably palladium acetate and tris(dibenzylideneacetone) dipalladium, and more preferably palladium acetate.

In some embodiments, the catalyst in step 6 described above is selected from the group consisting of palladium acetate and tris(dibenzylideneacetone) dipalladium, wherein the catalyst is used in the presence of a ligand selected from the group consisting of 2-dicyclohexylphosphonium-2',4',6'-triisopropylbiphenyl, 2-dicyclohexylphosphonium-2',6'-dimethoxybiphenyl, 2-dicyclohexylphosphonium-2',6'-diisopropoxy-1,1'-biphenyl, 4,5-bis(diphenylphosphino)-9,9-dimethylxanthene, 1,1'-binaphthol and 2,2'-bis-(diphenylphosphino)-1,1'-binaphthyl, preferably 4,5-bis (diphenylphosphino)-9,9-dimethylxanthene and 2-dicyclohexylphosphonium-2',4',6'-triisopropylbiphenyl, and more preferably 2-dicyclohexylphosphonium-2',4',6'-triisopropylbiphenyl.

In some embodiments, step 6 described above is conducted in the presence of palladium acetate, 2-dicyclohexylphosphonium-2',4',6'-triisopropylbiphenyl, the base and the solvent.

In some embodiments, the base in step 6 described above is selected from the group consisting of sodium carbonate, potassium carbonate, cesium carbonate, sodium acetate, potassium acetate, sodium ethoxide, sodium tert-butoxide, potassium tert-butoxide, triethylamine, pyridine, piperidine and N-methylpiperidine, preferably sodium carbonate, potassium carbonate and cesium carbonate, and more preferably cesium carbonate.

In some embodiments, the solvent in step 6 described above is selected from one of or a mixed solvent of two or more of dichloromethane, methanol, ethanol, isopropanol, tetrahydrofuran, dioxane, DMF, DMSO, toluene, ethylbenzene, ethylene glycol dimethyl ether, acetonitrile and water, preferably tetrahydrofuran and dioxane, and more preferably dioxane.

In some embodiments, the reaction temperature for step 6 described above is 80-150° C., preferably 80-120° C., and more preferably 100-120° C. In some specific embodiments, the reaction temperature for step 6 described above is about 110° C.

In some embodiments, the reaction time for step 6 described above is 3-10 hours, preferably 3-8 hours, and more preferably 4-6 hours. In some specific embodiments, the reaction time for step 6 described above is about 5 hours.

In some embodiments, the molar ratio of compound SMA-6 to compound SMA-10 in step 6 described above is 1:(1-2), preferably 1:(1-1.5), and more preferably 1:(1-1.2).

In some embodiments, the molar ratio of compound SMA-6 to the catalyst in step 6 described above is 1:(0.01-0.1), preferably 1:(0.02-0.06), and more preferably 1:(0.02-0.04).

In some embodiments, the molar ratio of compound SMA-6 to the ligand in step 6 described above is 1:(0.01-0.1), preferably 1:(0.02-0.06), and more preferably 1:(0.04-0.06).

In some embodiments, the molar ratio of compound SMA-6 to the base in step 6 described above is 1:(1-3), preferably 1:(1.5-3), and more preferably 1:(1.5-2).

In some embodiments, the molar-to-volume ratio of compound SMA-6 to the solvent in step 6 described above is 1 mmol:(1-8) mL, preferably 1 mmol:(2-6) mL, and more preferably 1 mmol:(3-4) mL.

In some embodiments, step 6 described above comprises: reacting compound SMA-6 with compound SMA-10 in the presence of cesium carbonate, 1,4-dioxane, 2-dicyclohexylphosphonium-2',4',6'-triisopropylbiphenyl and palladium acetate at a temperature of 110° C. to give compound SMA-7.

In some embodiments, step 6 described above further comprises: adding dichloromethane to the reaction system after the reaction is completed; and further comprises: adding sodium sulfate and a sulfydryl silica gel, stirring and filtering.

In some embodiments, step 6 described above further comprises: slurrying compound SMA-7 with ethyl acetate for treatment.

In the present application, compound SMA-10 may be prepared by reference to the method disclosed in Patent No. WO2018045993.

In the present application, compound SMA-10 is also commercially available.

In some embodiments, step 7 is conducted in the presence of an acid and a solvent.

In some embodiments, the acid in step 7 is selected from hydrogen chloride, and the solvent in step 7 is selected from the group consisting of methanol, ethanol and isopropanol, and preferably methanol.

In some specific embodiments, the acid in step 7 is selected from hydrogen chloride, and the solvent in step 7 is selected from methanol. In step 7, after the removal of the protecting group from compound SMA-7, a hydrochloride of the compound of formula (I) is obtained; the hydrochloride of the compound of formula (I) is then neutralized with a base for dissociation to give the compound of formula (I). In some embodiments, the base for neutralization of the hydrochloride of the compound of formula (I) is selected from the group consisting of an aqueous sodium hydroxide solution, an aqueous potassium hydroxide solution, an aqueous sodium carbonate solution and an aqueous potassium carbonate solution, and preferably an aqueous sodium hydroxide solution. In the present application, the deprotection reaction of compound SMA-7 to give the compound of formula (I) may further be conducted by reference to the method disclosed in Example 3 of Patent No. WO201614188.

The present application further provides a method for preparing intermediate SMA-6, comprising: step 1: reacting compound SMA-1 with compound SMA-8 to give compound SMA-2;

step 2: reacting compound SMA-2 with hydrazine hydrate to give compound SMA-3;

step 3: subjecting compound SMA-3 to a methylation reaction to give compound SMA-4;

step 4: reacting compound SMA-4 with bis(pinacolato) diboron to give compound SMA-5; and step 5: reacting compound SMA-5 with compound SMA-9 to give compound SMA-6.

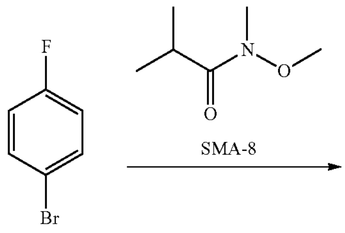

SMA-8

SMA-1

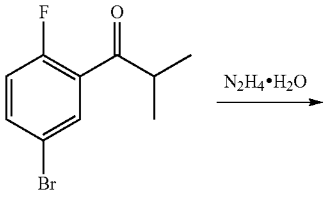

SMA-2

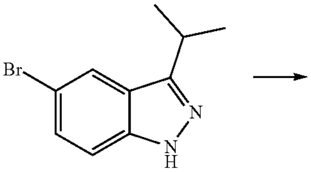

SMA-3

-continued

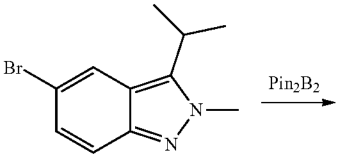

SMA-4

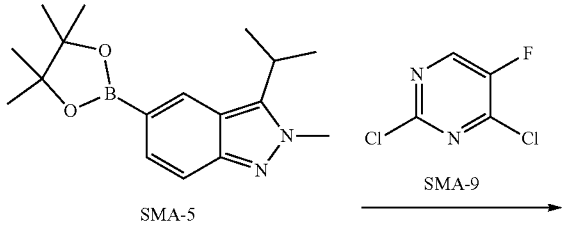

SMA-9

SMA-5

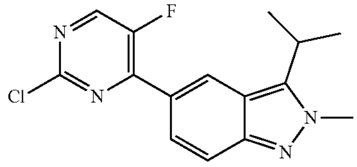

SMA-6

In some embodiments, the reaction conditions for steps 1, 2, 3, 4 and 5 in the method for preparing intermediate SMA-6 described above are as described in the steps 1, 2, 3, 4 and 5 in the method for preparing the compound of formula (I) in the present application.

The present application further provides use of the method for preparing intermediate SMA-6 in preparing a compound of formula (I).

The present application further provides a method for preparing intermediate SMA-3, comprising:

step 1: reacting compound SMA-1 with compound SMA-8 to give compound SMA-2; and step 2: reacting compound SMA-2 with hydrazine hydrate to give compound SMA-3.

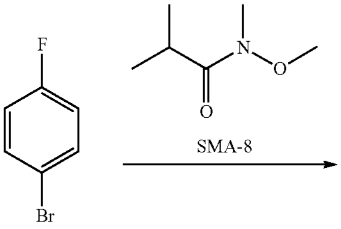

SMA-8

SMA-1

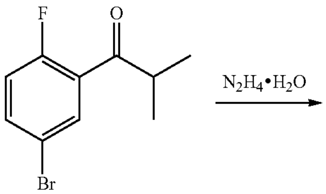

SMA-2

-continued

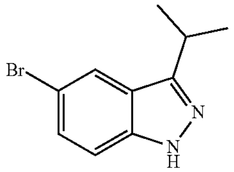

SMA-3

In some embodiments, the reaction conditions for steps 1 and 2 in the method for preparing intermediate SMA-3 described above are as described in the steps 1 and 2 in the method for preparing the compound of formula (I) in the present application.

The present application further provides use of the method for preparing intermediate SMA-3 described above in preparing a compound of formula (I).

The present application further provides a method for preparing intermediate SMA-4, comprising: subjecting compound SMA-3 to a methylation reaction to give compound SMA-4.

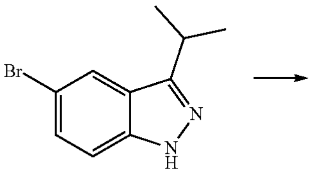

SMA-3

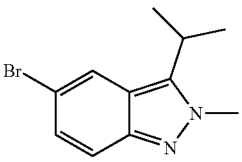

SMA-4

In some embodiments, the reaction conditions in the method for preparing intermediate SMA-4 described above are as described in the step 3 in the method for preparing the compound of formula (I) in the present application.

In one specific embodiment, the method for preparing intermediate SMA-4 comprises: reacting compound SMA-3 with trimethyloxonium tetrafluoroborate to give an onium salt intermediate compound SMA-3' (a tetrafluoroborate salt of compound SMA-4), and further hydrolyzing the onium salt intermediate compound SMA-3' to give compound SMA-4.

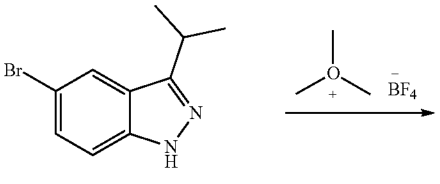

SMA-3

-continued

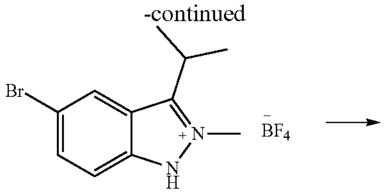

SMA-3'

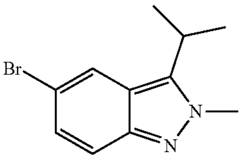

SMA-4

In some embodiments, the generation of the onium salt intermediate compound SMA-3' described above is conducted in the presence of a solvent.

In some embodiments, the solvent for the generation of the onium salt intermediate compound SMA-3' described above is selected from the group consisting of ethyl acetate and acetone, and preferably ethyl acetate.

In some embodiments, the reaction temperature for the generation of the onium salt intermediate compound SMA-3' described above is controlled at 10-30° C., preferably 20-30° C., and more preferably 25-30° C.

In some embodiments, the reaction time for the generation of the onium salt intermediate compound SMA-3' described above is 5-12 hours, preferably 8-12 hours, and more preferably 8-10 hours.

In some embodiments, in the generation of the onium salt intermediate compound SMA-3' described above, the molar ratio of compound SMA-3 to trimethyloxonium tetrafluoroborate is 1:(1-3), preferably 1:(1-2), and more preferably 1:(1-1.2).

In some embodiments, in the generation of the onium salt intermediate compound SMA-3' described above, the molar-to-volume ratio of compound SMA-3 to the solvent is 1 mmol:(1-5) mL, preferably 1 mmol:(2-4) mL, and more preferably 1 mmol:(2-3) mL.

In some embodiments, the hydrolysis of the onium salt intermediate compound SMA-3' described above is conducted in the presence of a base and a solvent.

In some embodiments, the base for the hydrolysis of the onium salt intermediate compound SMA-3' described above is selected from the group consisting of potassium carbonate, sodium carbonate, potassium bicarbonate, sodium bicarbonate, sodium hydroxide and potassium hydroxide, preferably sodium bicarbonate and sodium hydroxide, and more preferably sodium bicarbonate.

In some embodiments, the base for the hydrolysis of the onium salt intermediate compound SMA-3' described above is an aqueous solution thereof.

In some embodiments, the solvent for the hydrolysis of the onium salt intermediate compound SMA-3' described above is the same as the solvent for the generation of the onium salt intermediate described above.

In some embodiments, the solvent for the hydrolysis of the onium salt intermediate compound SMA-3' described above is selected from the group consisting of dichloromethane and ethyl acetate, preferably dichloromethane.

In some embodiments, the solvents required by the generation and hydrolysis of the onium salt intermediate compound SMA-3' described above are the same or different.

In some embodiments, the molar ratio of the onium salt intermediate compound SMA-3' described above to the base is 1:(1-5), preferably 1:(1-3), and more preferably 1:(2-3).

In some embodiments, the reaction time for the hydrolysis of the onium salt intermediate compound SMA-3' described above is 0.5-3 hours, and preferably 0.5-1 hour.

The present application further provides use of the method for preparing intermediate SMA-4 described above in preparing a compound of formula (I).

The preparation of the compound of formula (I) disclosed herein may further comprise purification of crude products.

In the present application, compound SMA-1, hydrazine hydrate, bis(pinacolato)diboron and compound SMA-9 are commercially available.

The methods for preparing the compound of formula (I) and the intermediate thereof provided herein have the following advantages:

(i) The intermediates prepared according to the present application do not require silica gel column chromatography in the post-treatment, featuring convenience, cost-efficiency and availability.

(ii) Compared with the prior art, in the preparation of the compound of formula (I) disclosed herein, the number of reaction steps and the amount of the metal catalyst used are both reduced, which is more cost-efficient, and the metal residues in the final product are correspondingly less.

(iii) Compared with the prior art, the preparation of the compound of formula (I) disclosed herein reduces the steps of allyl reduction, greatly shortens the reaction time, avoids the use of a rhodium catalyst, and is more cost-efficient and environment-friendly.

(iv) The preparation of the compound of formula (I) disclosed herein has cheap and readily available starting materials and reagents, greatly simplified reaction process, shortened reaction time, improved total yield and a high purity of the key intermediate and final product, being suitable for industrial production.

In the present application, LDA refers to lithium diisopropylamide; DMF refers to N,N-dimethylformamide; DMSO refers to dimethyl sulfoxide; DBU refers to 1,8-diazabicycloundec-7-ene; DMAP refers to 4-dimethylaminopyridine; $Pin_2B_2$ refers to bis(pinacolato)diboron; $Pd(dppf)Cl_2$ refers to 1,1'-bis(diphenylphosphino) ferrocenepalladium dichloride; TLC refers to thin layer chromatography; HPLC refers to high-performance liquid chromatography.

DETAILED DESCRIPTION

The following specific examples are presented to enable those skilled in the art to more clearly understand and implement the present application. These specific examples should not be considered as limit to the present application, but merely as exemplary description and representative of the present application.

The chemical reactions of the embodiments disclosed herein are conducted in a proper solvent that must be suitable for the chemical changes in the present application and the reagents and materials required. In order to acquire the compounds disclosed herein, it is sometimes necessary for those skilled in the art to modify or select a synthesis procedure or a reaction process based on the existing embodiments.

All solvents used in the present application are commercially available and can be used without further purification.

Preparation of Compound SMA-8

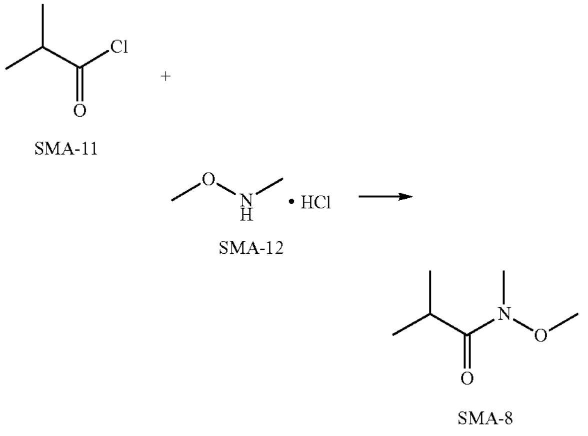

SMA-11

SMA-12

SMA-8

5.0 kg of N,O-dimethylhydroxylamine hydrochloride (SMA-12) was added into a 100 L reaction kettle, followed by the addition of dichloromethane (26 L). The resulting mixture was stirred for dissolution and cooled to an internal temperature of −5 to 5° C. Triethylamine (10.4 kg) was slowly and dropwise added with the internal temperature maintained below 5° C. After the addition is completed, isobutyryl chloride (SMA-11) (5.46 kg) was added dropwise, with the internal temperature maintained below 5° C. After the addition, the reaction solution was stirred for reaction at room temperature for 1 hour. The reaction of the starting material isobutyryl chloride was completed as detected by TLC, the reaction solution was slowly poured into a saturated aqueous sodium bicarbonate solution (77 L), and the phases were separated. The organic phase was sequentially washed with 1 mol/L hydrochloric acid (26 L) and a 10% aqueous sodium chloride solution (26 L), dried over anhydrous sodium sulfate and filtered. The filtrate was concentrated at reduced pressure to give compound SMA-8 (5.5 kg, 81.8% yield).

Preparation of Compound of Formula (I)

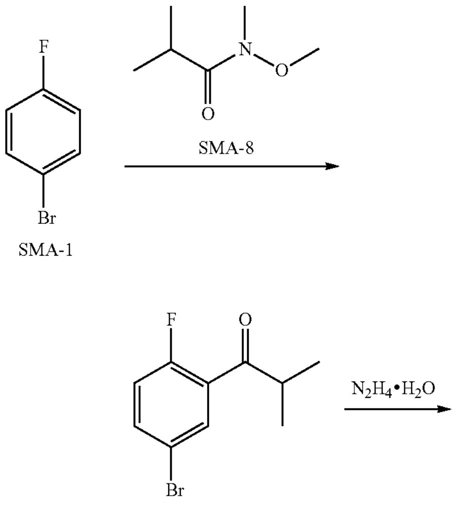

SMA-8

SMA-1

SMA-2

-continued

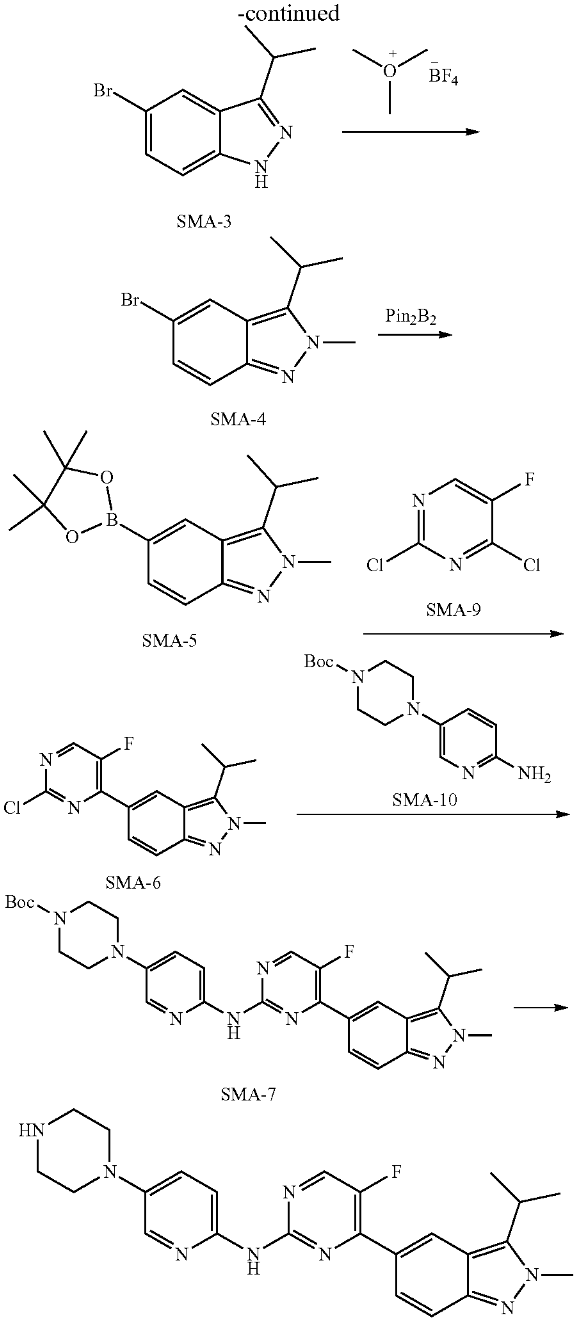

SMA-3

SMA-4

SMA-5

SMA-9

SMA-10

SMA-6

SMA-7

(1)

Preparation of Compound SMA-2

To a 100-L stainless steel reaction kettle were added p-fluorobromobenzene (SMA-1) (4 kg), N,O-dimethyl-isobutyramide (SMA-8) (4.0 kg) and tetrahydrofuran (23.2 L). The resulting mixture was stirred for complete dissolution and cooled to an internal temperature of −75 to −65° C. LDA (2 mol/L, 23.2 L) was slowly and dropwise added with the internal temperature maintained below −65° C. After the addition, the reaction solution was stirred for reaction for 3 hours, with the internal temperature maintained at −75 to −65° C. A 1 mol/L aqueous hydrochloric acid solution (46 L) was added dropwise into the reaction solution. The mixture was slowly heated to room temperature after the addition, and the phases were separated. The aqueous phase was extracted with ethyl acetate (15 L), and the organic phases were combined, washed with water (10 L×3), dried over anhydrous sodium sulfate and filtered. The filtrate was concentrated to dryness at reduced pressure to give compound SMA-2 (6.18 kg, 85.7% yield).

Preparation of Compound SMA-3

To a 50 L reaction kettle were added compound SMA-2 (6.0 kg), ethylene glycol (23 L) and 80% hydrazine hydrate (2.4 kg). After the addition, the resulting mixture was stirred at reflux for reaction for 2 hours. The water in the reaction system was removed, and the reaction was conducted at 150° C. for 10 hours. The reaction system was slowly cooled to room temperature, and 23 L of purified water was added. The mixture was stirred for crystallization for 1 hour and filtered. The filter cake was slurried with 25 L of purified water, filtered, and dried by air blasting at 50° C. to give compound SMA-3 (3.2 kg, 70% yield).

Preparation of Compound SMA-4

To a 50 L reaction kettle were added compound SMA-3 (3 kg) and ethyl acetate (30 L), followed by the addition of trimethyloxonium tetrafluoroborate (2.06 kg) in nitrogen atmosphere. After the addition, the resulting mixture was stirred for reaction at 25-30° C. for 8 hours and filtered by centrifugation. The filter cake was slurried with 40 L of n-hexane for 3 hours, filtered by centrifugation, and dried by air blasting to give a tetrafluoroborate salt of compound SMA-4 (SMA-3') (3.3 kg, 77.1% yield).

The tetrafluoroborate salt (135 g) of compound SMA-4 described above was added to a 5 L beaker, followed by addition of 1 L of saturated $NaHCO_3$ solution and 1 L of dichloromethane. The resulting mixture was stirred for 0.5 hour, and the phases were separated. The organic phase was washed once with 500 mL of saturated NaCl solution and separated. The organic phase was concentrated to dryness to give compound SMA-4 for later use.

Preparation of Compound SMA-5

The compound SMA-4 obtained as described above, 1,4-dioxane (500 mL), bis(pinacolato)diboron (151 g) and potassium acetate (78 g) were added into a 1 L four-necked flask. The resulting mixture was degassed and purged with nitrogen three times, and $Pd(dppf)Cl_2CH_2Cl_2$ (1.5 g) was added in nitrogen atmosphere. The system was heated to an internal temperature of 90-95° C. after the addition, stirred for reaction for 9 hours, then cooled to room temperature, filtered, and rinsed with 1,4-dioxane (50 mL) to give a filtrate containing compound SMA-5 for later use.

Preparation of Compound SMA-6

The filtrate containing compound SMA-5 was transferred to a 1 L four-necked flask, and 2,4-dichloro-5-fluoropyrimidine (SMA-9) (68 g) and potassium carbonate (111 g) were sequentially added, followed by addition of 100 mL of purified water under stirring. The resulting mixture was degassed and purged with nitrogen three times, and $Pd(dppf)Cl_2CH_2Cl_2$ (3.3 g) was added in nitrogen atmosphere. The system was heated to an internal temperature of 90-95° C. after the addition, stirred for reaction for 12 hours, then cooled to room temperature, concentrated, slurried with 500 mL of an aqueous ethanol solution (ethanol/water=1/1) for 1 hour and filtered. The solid was added to a mixed system of 500 mL of water and 300 mL of dichloromethane and stirred for dissolution, and the phases were separated. The aqueous phase was extracted with dichloromethane (100 mL×2). The organic phases were combined. Anhydrous $Na_2SO_4$ and 3% activated carbon were added for dehydration drying and decolorization for 0.5 hour. The resulting mixture was filtered. The filtrate was concentrated to dryness to give a crude product (75 g), and the crude product was slurried with ethyl acetate (200 mL) for 0.5 hour, filtered and dried to give a pure product of compound SMA-6 (60 g, 99.1% purity, 50.1% yield).

Preparation of Compound SMA-7

Compound SMA-6 (1.70 kg), compound SMA-10 (1.57 kg), cesium carbonate (3.61 kg), 1,4-dioxane (17 L), 2-dicyclohexylphosphonium-2',4',6'-triisopropylbiphenyl (158.39 g) and palladium acetate (37.30 g) were sequentially added into a 50 L reaction kettle in nitrogen atmosphere. The system was stirred at 110° C. for 5 hours and cooled. 20 L of dichloromethane was added to the reaction mixture, and the mixture was stirred for 30 minutes, filtered through diatomite, and washed twice with water. Sodium sulfate and a sulfydryl silica gel (5%) were added, and the mixture was stirred and filtered. A 5% sulfydryl silica gel was added to the filtrate, and the mixture was stirred and filtered. The resulting filtrate was concentrated to dryness, slurried with ethyl acetate (17 L) for 2 hours, filtered, and dried to give compound SMA-7, which was directly used in the next reaction.

Preparation of Compound of Formula (I)

1.9 kg of hydrogen chloride gas was introduced into a methanol (12.5 L) solution to give a 4 M hydrogen chloride/methanol solution. Methanol (12.5 L) and compound SMA-7 were sequentially added into a reaction kettle at 20° C. to give a suspension. Then 12.5 L of the 4 M hydrogen chloride/methanol solution was added into a 50 L reaction kettle, and the temperature of the system was raised to 50° C. After 10 minutes, a solid was precipitated and a large amount of gas was generated. The reaction system was stirred at 50° C. for 17.5 hours. After the reaction was completed as indicated by TLC, the reaction mixture was cooled to 20° C. and filtered, and the filter cake was washed with 5 L of methanol. The resulting filter cake was dried in a vacuum oven at 50° C. for 42 hours to give a crude hydrochloride of the compound of formula (I), which was directly used in the next reaction.

2.60 kg of the crude hydrochloride of the compound of formula (I) and 7.8 L of ethanol were sequentially added into a 50 L reaction kettle at 20° C., and the resulting turbid solution was heated to 75° C. 12.4 L of a 5% aqueous sodium hydroxide solution was added dropwise into the reaction kettle, the pH value was adjusted to about 11, and the reaction system was cooled to 68° C. After about 5 minutes, a solid was precipitated. The reaction system was heated to 75° C., stirred at that temperature for 1 hour, then cooled to 20° C. and filtered. The filter cake was washed with water (10 L×2), and the resulting filter cake was dried in a vacuum oven at 60° C. for 48 hours to give compound of formula (I) (1.9 kg, 83.4% yield, 98.9% purity).

The invention claimed is:

1. A method for preparing a compound of formula (I), comprising:

step 1: reacting compound SMA-1 with compound SMA-8 to give compound SMA-2;

step 2: reacting compound SMA-2 with hydrazine hydrate to give compound SMA-3;

step 3: subjecting compound SMA-3 to a methylation reaction to give compound SMA-4;

step 4: reacting compound SMA-4 with bis(pinacolato) diboron to give compound SMA-5;

step 5: reacting compound SMA-5 with compound SMA-9 to give compound SMA-6;

step 6: reacting compound SMA-6 with compound SMA-10 to give compound SMA-7; and step 7: reacting compound SMA-7 to give compound of formula (I);

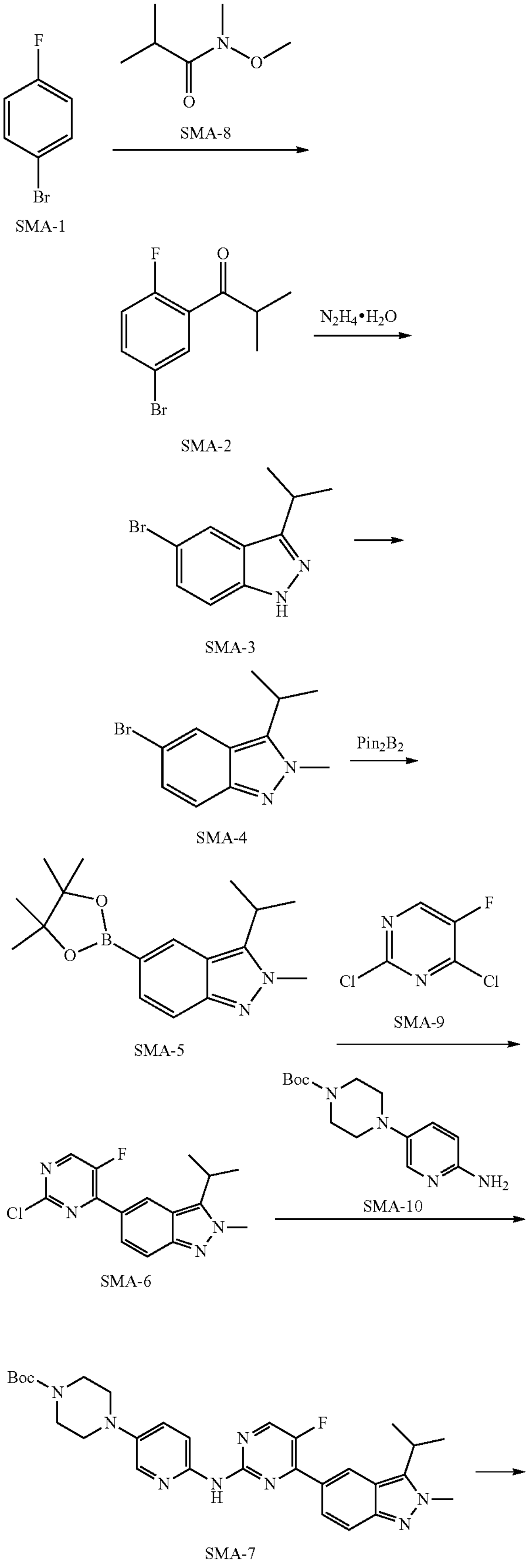

SMA-1, SMA-8, SMA-2, SMA-3, SMA-4, SMA-5, SMA-9, SMA-6, SMA-10, SMA-7

-continued

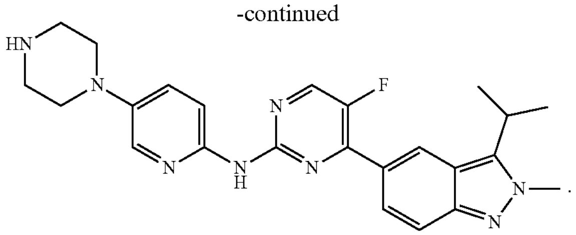

(1)

2. The method for preparing the compound of formula (I) according to claim 1, wherein step 1 is conducted in the presence of a solvent and a base; wherein the solvent is selected from one of or a mixed solvent of two or more of dichloromethane, tetrahydrofuran, dioxane, DMF, DMSO, acetonitrile, diethyl ether, isopropyl ether, methyl tert-butyl ether, 2-methyltetrahydrofuran, n-hexane and n-heptane; and the base is selected from the group consisting of n-butyllithium, tert-butyllithium, sodium tert-butoxide, potassium tert-butoxide, lithium diisopropylamide, lithium hexamethyldisilazide, sodium bis(trimethylsilyl) amide, sodium hydride and lithium hydroxide.

3. The method for preparing the compound of formula (I) according to claim 2, wherein the molar ratio of compound SMA-1 to compound SMA-8 is 1:(1-2).

4. The method for preparing the compound of formula (I) according to claim 2, wherein the molar-to-volume ratio of compound SMA-1 to the solvent is 1 mmol:(0.5-1.5) mL.

5. The method for preparing the compound of formula (I) according to claim 2, wherein the molar ratio of compound SMA-1 to the base is 1:(1-3).

6. The method for preparing the compound of formula (I) according to claim 1, wherein step 2 is conducted in the presence of a solvent; wherein the solvent is selected from the group consisting of ethylene glycol, N,N-dimethylformamide (DMF), dimethyl sulfoxide (DMSO), diphenyl ether, orthodichlorobenzene, sulfolane, trimethylbenzene, diethylene glycol dimethyl ether and N-methylpyrrolidone.

7. The method for preparing the compound of formula (I) according to claim 6, wherein the molar ratio of compound SMA-2 to hydrazine hydrate is 1:(1-3).

8. The method for preparing the compound of formula (I) according to claim 5, wherein the molar-to-volume ratio of compound SMA-2 to the solvent is 1 mmol:(0.5-1.5) mL.

9. The method for preparing the compound of formula (I) according to claim 1, wherein step 3 is conducted in the presence of a methylating agent and a solvent; wherein the methylating agent is selected from the group consisting of iodomethane, dimethyl sulfate, dimethyl carbonate, methyl p-toluenesulfonate, methyl triflate, tetramethylammonium fluoride, trimethyl phosphate, trimethyloxonium tetrafluoroborate and 1-methyl-3-p-tolyltriazole; and the solvent is selected from one of or a mixed solvent of two or more of ethyl acetate, dichloromethane and acetone.

10. The method for preparing the compound of formula (I) according to claim 9, wherein the molar ratio of compound SMA-3 to the methylating agent is 1:(1-3); and the molar ratio of compound SMA-3 to the base is 1:(1-5).

11. The method for preparing the compound of formula (I) according to claim 1, wherein step 4 is conducted in the presence of a catalyst, a base and a solvent; wherein the catalyst is selected from the group consisting of palladium acetate, 1,2-bis(diphenylphosphonyl) ethane palladium dichloride, 1,3-bis(diphenylphosphino) propane palladium dichloride, 1,4-bis(diphenylphosphino) butane palladium dichloride, bis(triphenylphosphine) palladium dichloride, bis(cyanophenyl) palladium dichloride, 1,1'-bis(diphenylphosphino) ferrocenepalladium dichloride and tris(dibenzylideneacetone) dipalladium;

the base is selected from the group consisting of sodium carbonate, potassium carbonate, cesium carbonate, sodium acetate, potassium acetate, sodium ethoxide, sodium tert-butoxide, potassium tert-butoxide, triethylamine, pyridine, piperidine and N-methylpiperidine; and the solvent is selected from one of or a mixed solvent of two or more of methanol, ethanol, isopropanol, tetrahydrofuran, dioxane, DMF, DMSO, toluene, ethylbenzene, ethylene glycol dimethyl ether, acetonitrile and water.

12. The method for preparing the compound of formula (I) according to claim 11, wherein the molar ratio of compound SMA-4 to bis(pinacolato) diboron is 1:(1-3);

the molar ratio of compound SMA-4 to the catalyst is 1:(0.001-0.01);

the molar ratio of compound SMA-4 to the base is 1:(1-3); and the molar-to-volume ratio of compound SMA-4 to the solvent is 1 mmol:(1-2) mL.

13. The method for preparing the compound of formula (I) according to claim 1, wherein step 5 is conducted in the presence of a catalyst, a base and a solvent; wherein the catalyst is selected from the group consisting of palladium acetate, 1,2-bis(diphenylphosphonyl) ethane palladium dichloride, 1,3-bis(diphenylphosphino) propane palladium dichloride, 1,4-bis(diphenylphosphino) butane palladium dichloride, bis(triphenylphosphine) palladium dichloride, bis(cyanophenyl) palladium dichloride, 1,1'-bis(diphenylphosphino) ferrocenepalladium dichloride and tris(dibenzylideneacetone) dipalladium;

the base is selected from the group consisting of sodium carbonate, potassium carbonate, cesium carbonate, sodium acetate, potassium acetate, sodium ethoxide, sodium tert-butoxide, potassium tert-butoxide, triethylamine, pyridine, piperidine and N-methylpiperidine; and the solvent is selected from one of or a mixed solvent of two or more of methanol, ethanol, isopropanol, tetrahydrofuran, dioxane, DMF, DMSO, toluene, ethylbenzene, ethylene glycol dimethyl ether, acetonitrile and water.

14. The method for preparing the compound of formula (I) according to claim 13, wherein the molar ratio of compound SMA-5 to compound SMA-9 is 1:(1-2);

the molar ratio of compound SMA-5 to the catalyst is 1:(0.005-0.05);

the molar ratio of compound SMA-5 to the base is 1:(1-3); and the molar-to-volume ratio of compound SMA-5 to the solvent is 1 mmol:(0.1-2) mL.

15. The method for preparing the compound of formula (I) according to claim 1, wherein step 6 is conducted in the presence of a catalyst, a base and a solvent; wherein the catalyst is selected from the group consisting of palladium acetate, 1,2-bis(diphenylphosphonyl) ethane palladium dichloride, 1,3-bis(diphenylphosphino) propane palladium dichloride, 1,4-bis(diphenylphosphino) butane palladium dichloride, bis(triphenylphosphine) palladium dichloride, bis(cyanophenyl) palladium dichloride, 1,1'-bis(diphenylphosphino) ferrocenepalladium dichloride and tris(dibenzylideneacetone) dipalladium;

the base is selected from the group consisting of sodium carbonate, potassium carbonate, cesium carbonate, sodium acetate, potassium acetate, sodium ethoxide, sodium tert-butoxide, potassium tert-butoxide, triethylamine, pyridine, piperidine and N-methylpiperidine; and the solvent is selected from one of or a mixed solvent of two or more of dichloromethane, methanol, ethanol, isopropanol, tetrahydrofuran, dioxane, DMF, DMSO, toluene, ethylbenzene, ethylene glycol dimethyl ether, acetonitrile and water.

16. The method for preparing the compound of formula (I) according to claim 15, wherein the molar ratio of compound SMA-6 to compound SMA-10 is 1:(1-2);

the molar ratio of compound SMA-6 to the catalyst is 1:(0.01-0.1);

the molar ratio of compound SMA-6 to a ligand is 1:(0.01-0.1);

the molar ratio of compound SMA-6 to the base is 1:(1-3); and the molar-to-volume ratio of compound SMA-6 to the solvent is 1 mmol:(1-8) mL.

17. The method for preparing the compound of formula (I) according to claim 15, wherein step 6 further comprises: adding dichloromethane to the reaction system after the reaction is completed; and further comprises: adding sodium sulfate and a sulfhydryl silica gel, stirring and filtering;

or step 6 further comprises: slurrying compound SMA-7 with ethyl acetate for treatment.

18. The method for preparing the compound of formula (I) according to claim 1, wherein step 7 is conducted in the presence of an acid and a solvent; wherein the acid is hydrogen chloride, and the solvent is selected from the group consisting of methanol, ethanol and isopropanol.

19. A method for preparing intermediate SMA-6, comprising:

step 1: reacting compound SMA-1 with compound SMA-8 to give compound SMA-2;

step 2: reacting compound SMA-2 with hydrazine hydrate to give compound SMA-3;

step 3: subjecting compound SMA-3 to a methylation reaction to give compound SMA-4;

step 4: reacting compound SMA-4 with bis(pinacolato) diboron to give compound SMA-5; and step 5: reacting compound SMA-5 with compound SMA-9 to give compound SMA-6;

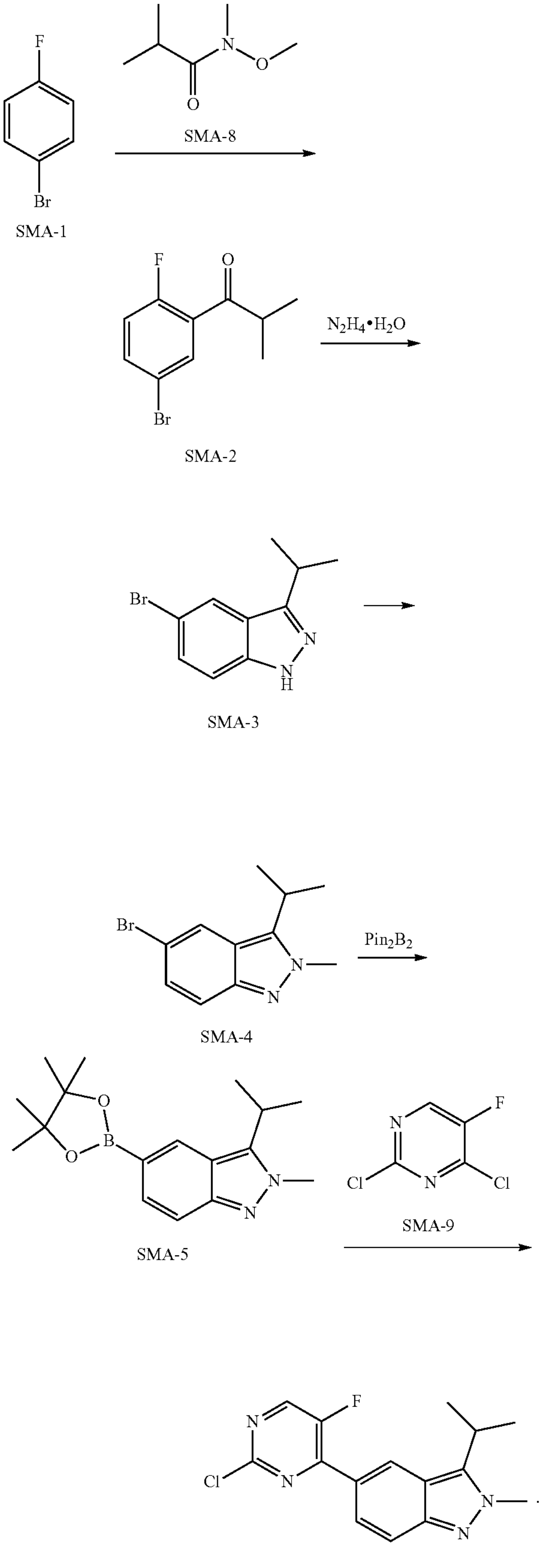

SMA-1
SMA-2
SMA-3
SMA-4
SMA-5
SMA-6

20. A method for preparing a compound of formula (I) which comprises the steps of preparing intermediate SMA-6 according to claim 19, and reacting compound SMA-6 with a compound to give the compound of formula (I):
(1)
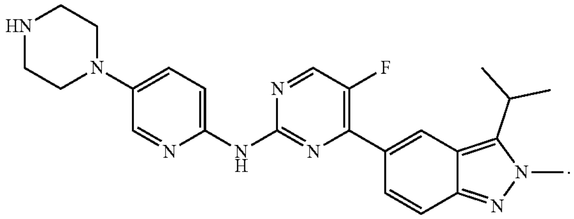
* * * * *